US010058341B2

(12) United States Patent
Okada

(10) Patent No.: US 10,058,341 B2
(45) Date of Patent: Aug. 28, 2018

(54) ENDOSCOPIC TREATMENT INSTRUMENT

(71) Applicant: OLYMPUS CORPORATION, Hachioji-shi, Tokyo (JP)

(72) Inventor: Tsutomu Okada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/599,845

(22) Filed: May 19, 2017

(65) Prior Publication Data

US 2017/0252052 A1  Sep. 7, 2017

Related U.S. Application Data

(63) Continuation of application No. PCT/JP2015/081167, filed on Nov. 5, 2015.

(30) Foreign Application Priority Data

Mar. 25, 2015  (JP) ................. 2015-062429

(51) Int. Cl.
A61B 17/221 (2006.01)
A61B 1/00 (2006.01)
A61B 17/00 (2006.01)

(52) U.S. Cl.
CPC ........ A61B 17/221 (2013.01); A61B 1/00085 (2013.01); A61B 2017/0034 (2013.01);
(Continued)

(58) Field of Classification Search
CPC ........ A61B 17/221; A61B 2017/00323; A61B 2017/0034; A61B 2017/2212;
(Continued)

(56) References Cited

U.S. PATENT DOCUMENTS 6,077,274 A    6/2000 Ouchi et al.
6,245,078 B1 * 6/2001 Ouchi .............. A61B 17/32056
                                                606/113

FOREIGN PATENT DOCUMENTS

EP    2 638 870 A1   9/2013
JP    S56-109705 U   8/1981
(Continued)

OTHER PUBLICATIONS

Nov. 1, 2016 Office Action issued in Japanese Patent Application No. 2016-555642.
(Continued)

Primary Examiner — Ryan J Severson
Assistant Examiner — Christian Knauss
(74) Attorney, Agent, or Firm — Oliff PLC

(57) ABSTRACT

An endoscopic treatment instrument includes a sheath; a basket section formed by elastic wires; a manipulation wire connected to the basket section; and a distal end cover attached to a distal end of the sheath. The distal end cover has: a first opening; a second opening; an inner peripheral surface disposed between the first and second opening; and a curved surface bent over the whole circumference in t circumference direction of the distal end cover. Each of the plurality of the elastic wires has: a proximal end portion, a distal end portion, and a maximum diameter section. A radius of curvature of the curved surface is smaller than a radius of curvature of each of the plurality of the elastic wires. A contact position of the elastic wires and the curved surface moves in accordance with a retraction of the elastic wires.

4 Claims, 16 Drawing Sheets

(52) U.S. Cl.
CPC ............... *A61B 2017/00323* (2013.01); *A61B 2017/2212* (2013.01)

(58) Field of Classification Search
CPC ............ A61B 1/00085; A61B 1/00089; A61B 1/00137; A61B 2017/00292; A61B 2017/00305; A61B 2017/00358; A61B 17/32056
See application file for complete search history.

(56) References Cited

FOREIGN PATENT DOCUMENTS

| | | |
|---|---|---|
| JP | S59-230545 A | 12/1984 |
| JP | S62-41724 B2 | 9/1987 |
| JP | H11-99157 A | 4/1999 |
| JP | 2006-314715 A | 11/2006 |
| JP | 2013-22386 A | 2/2013 |
| JP | 5252606 B2 | 7/2013 |
| WO | 2012/141213 A1 | 10/2012 |

OTHER PUBLICATIONS

Jan. 26, 2016 International Search Report issued in International Patent Application No. PCT/JP2015/081167.

\* cited by examiner

ENDOSCOPIC TREATMENT INSTRUMENT

This application is a continuation application based on a PCT International Application No. PCT/JP2015/081167, filed on Nov. 5, 2015, whose priority is claimed on Japanese Patent Application No. 2015-062429, filed on Mar. 25, 2015. The contents of both of the PCT International Application and the Japanese Patent Application are incorporated herein by reference.

BACKGROUND OF THE INVENTION

Field of the Invention

The present invention relates to an endoscopic treatment instrument.

Description of Related Art

In the related art, a basket forceps for collecting a calculus is known as an endoscopic treatment instrument that is attached to an endoscope to be used. The basket forceps for gathering a calculus is used for a treatment in which a calculus or the like is held and removed.

For example, Pamphlet of PCT International Publication No. WO2012/141213 discloses an endoscopic treatment instrument including a basket section formed by a plurality of elastic wires having a spiral shape.

A fragmentation device configured to fragment and remove a large calculus or the like in a body is also known. For example, Japanese Examined Patent Application, Second Publication No. S62-41724 discloses a fragmentation device having a coil-shaped flexible tube, a rigid distal end tip arranged on a distal end of the flexible tube, and a basket which is protruded from or retracted into an inside of the flexible tube.

The fragmentation device disclosed in Japanese Examined Patent Application, Second Publication No. S62-41724 has a plurality of clearance grooves configured to accommodate a plurality of basket wires forming a basket at a distal end tip thereof

SUMMARY OF THE INVENTION

According to a first aspect of the present invention, an endoscopic treatment instrument includes a sheath which is inserted through a channel of an endoscope; a basket section which is configured to be protruded from and retracted into the sheath, and is formed by a plurality of elastic wires with a spiral shape wound in a same direction; a manipulation wire connected to the basket section and inserted through the sheath to be advanceable and retractable with respect to the sheath; and a distal end cover which is attached to a distal end of the sheath, wherein the distal end cover has: a first opening which is open toward the sheath to communicate with inside of the sheath; a second opening which is open toward a side opposite to the first opening; an inner peripheral surface which is disposed between the first opening and the second opening, and has an inner diameter such that the plurality of the elastic wires are inserted through; and a curved surface which has a bent shape over the whole circumference in the circumference direction of the distal end cover such that an inner diameter of the curved surface increases gradually from the inner peripheral surface toward the second opening, and configured to slide the plurality of the elastic wires in the circumferential direction of the distal end cover, wherein each of the plurality of the elastic wires has: a proximal end portion connected to the manipulation wire; a distal end portion opposite to the proximal end portion; and a maximum diameter section configured to define a maximum outer diameter of the basket section between the proximal end portion and the distal end portion, wherein a radius of curvature of the curved surface at a cross section including a center line of the distal end cover is smaller than a radius of curvature of each of the plurality of the elastic wires between the proximal end portion and the maximum diameter section, and wherein a contact position of the plurality of the elastic wires and the curved surface moves toward a circumference direction of the distal end cover in accordance with a retraction movement of the plurality of the elastic wires into the sheath.

According to a second aspect of the present invention, in the endoscopic treatment instrument according to the first aspect, each of the plurality of the elastic wire may have a first curved section, a second curved section, and a third curved section disposed in this order between the proximal end portion and the maximum diameter section in a direction from the proximal end portion toward the maximum diameter section, the first curved section, the second curved section, and the third curved section at least having different one of radii of curvature and bent directions, and a radius of curvature of the third curved section may be smaller than any of a radius of curvature of the first curved section and a radius of curvature of the second curved section.

According to a third aspect of the present invention, in the endoscopic treatment instrument according to the first aspect, the distal end cover may have a plurality of projections projecting from the second opening in a center line direction of the distal end cover and arranged to have gaps in a circumferential direction of the distal end cover, and the curved surface may be provided between two projections disposed apart from each other in the circumferential direction of the distal end cover among the plurality of projections.

According to a fourth aspect of the present invention, in the endoscopic treatment instrument according to the third aspect, the projection may have a first lateral surface directed in a first direction in a circumferential direction of the distal end cover; and a second lateral surface directed in a direction opposite to the first direction in the circumferential direction of the distal end cover, and the first lateral surface and the second lateral surface which face each other at two projections disposed apart from each other in the circumferential direction of the distal end cover may have a gap with respect to an outer circumference side of the distal end cover wider than a gap with respect to an inner circumference side of the distal end cover, the first lateral surface and the second lateral surface extending in a spiral direction of the plurality of the elastic wires.

According to a fifth aspect of the present invention, in the endoscopic treatment instrument according to the third aspect, groove sections formed between the plurality of projections may be arranged apart from each other in the circumferential direction of the distal end cover, and a number of the groove sections may be smaller than the number of the plurality of elastic wires.

DETAILED DESCRIPTION OF THE INVENTION (First Embodiment)

Figure 1:
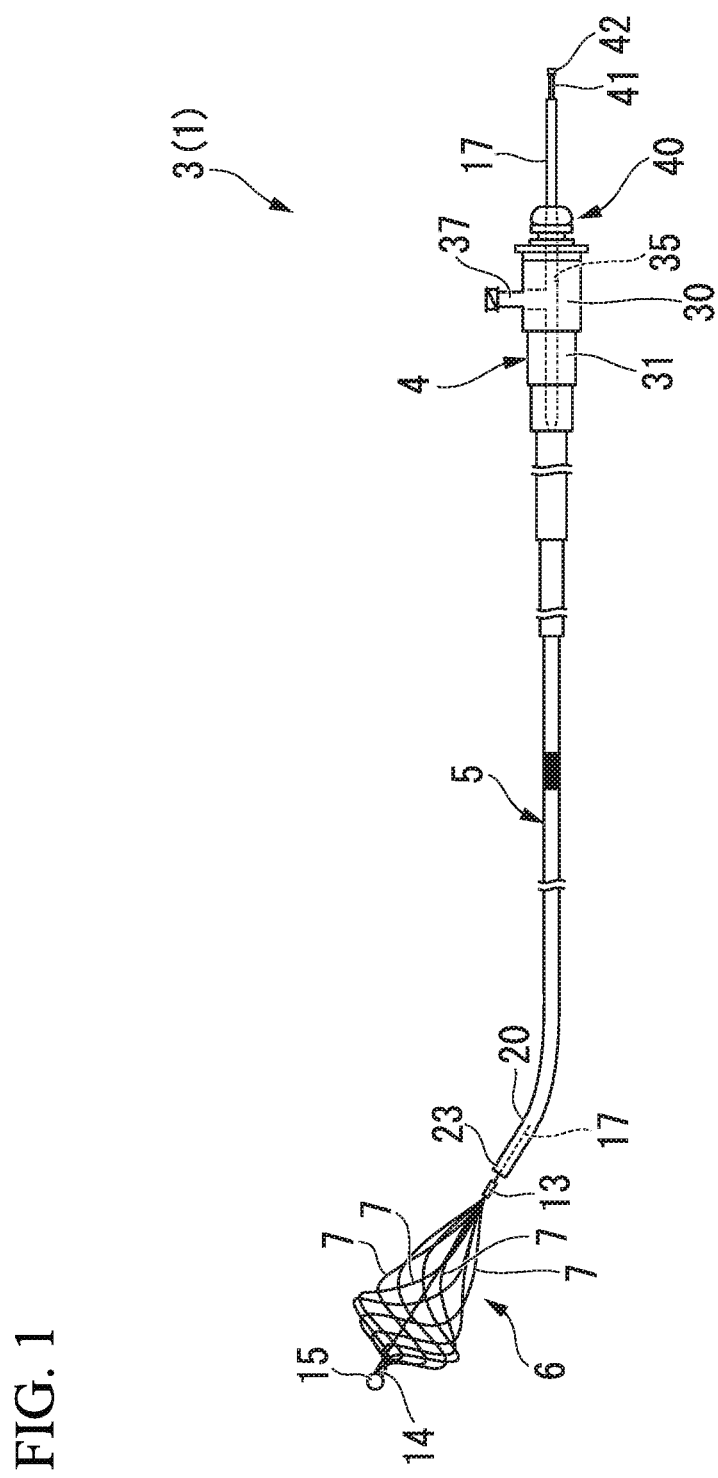
FIG. 1 is a side view showing a fragmentation tool in a calculus fragmentation device according to a first embodiment of the present invention.
Figure 2:
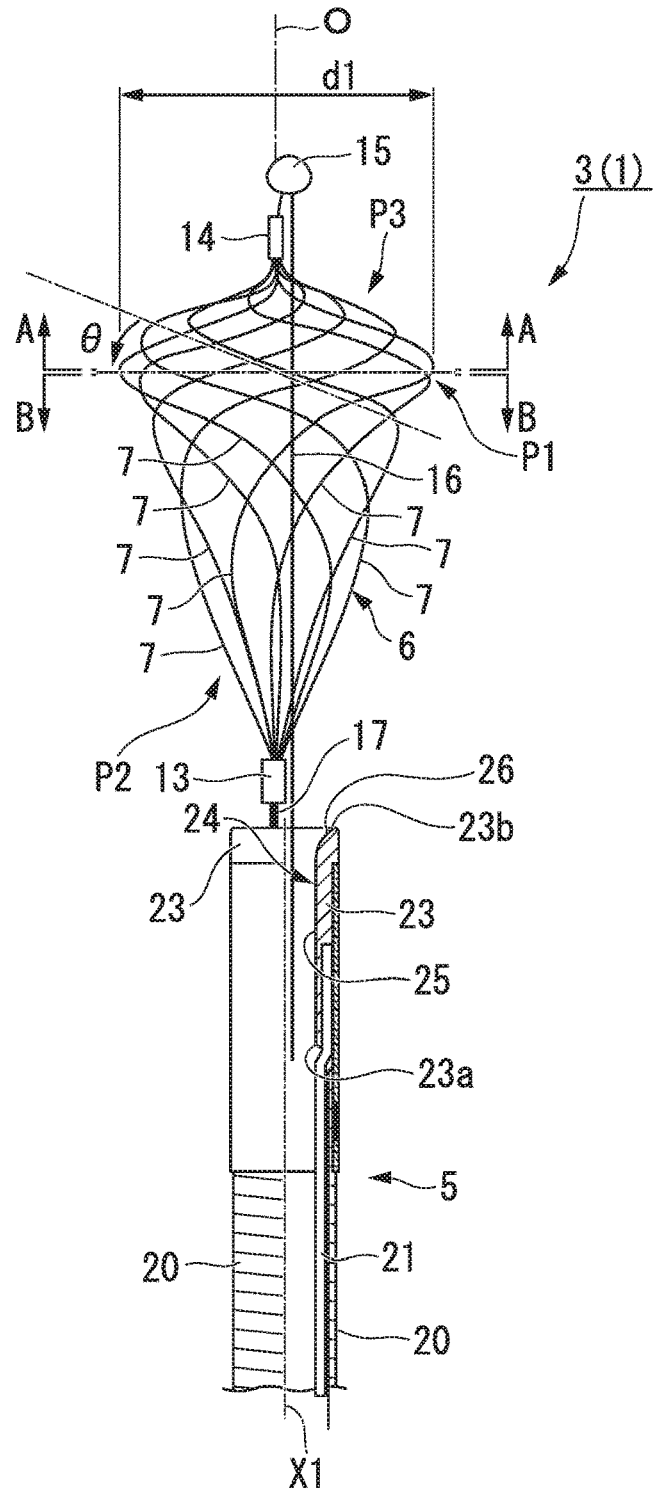
FIG. 2 is a partial cross-sectional enlarged view showing a configuration of a distal end portion of the fragmentation tool according to the first embodiment.
Figure 3:
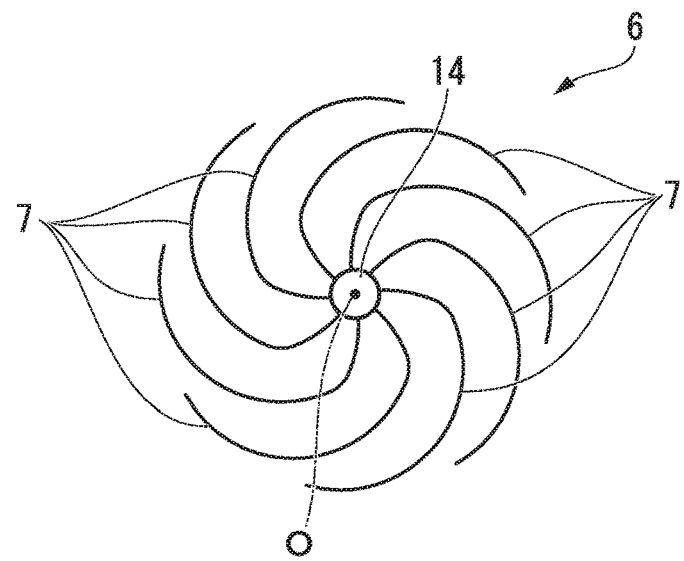
FIG. 3 is a cross-sectional view taken along line A-A of FIG. 2.
Figure 4:
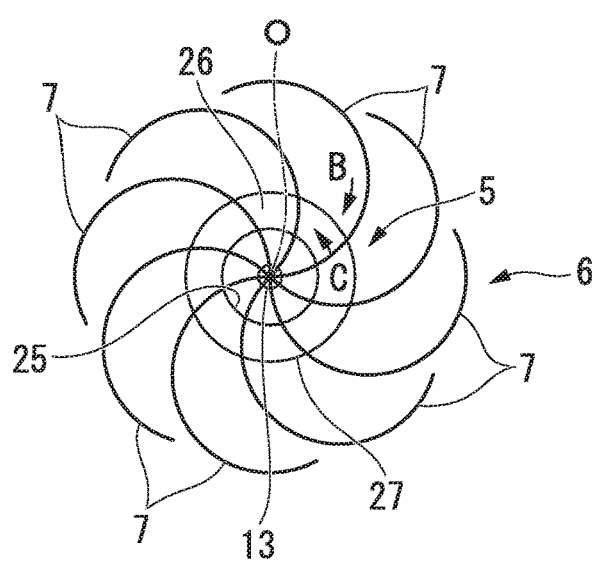
FIG. 4 is a cross-sectional view taken along line B-B of FIG. 2.
Figure 5:
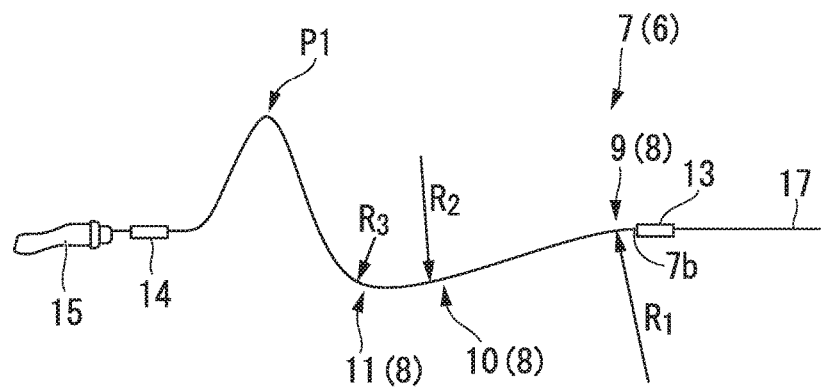
FIG. 5 is a schematic diagram showing a structure of elastic wires provided in a basket section of the fragmentation tool according to the first embodiment.
Figure 6:
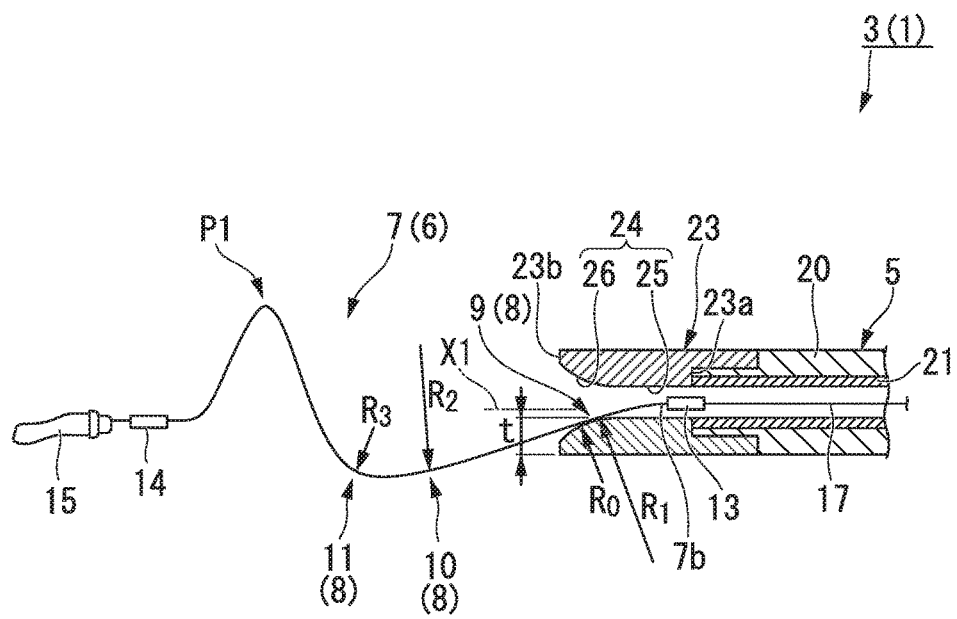
FIG. 6 is a partial cross-sectional view showing a relationship between shapes of a distal end cover and the elastic wire of the fragmentation tool according to the first embodiment.
Figure 7:
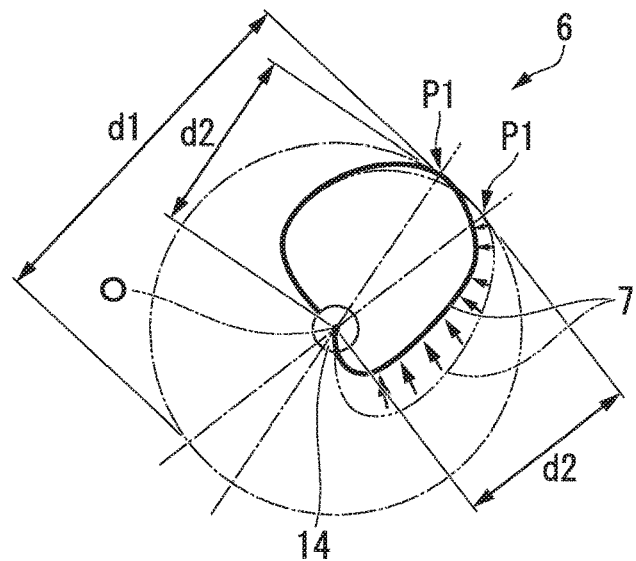
FIG. 7 is a schematic diagram for describing a function of the elastic wire according to the first embodiment.
Figure 8:
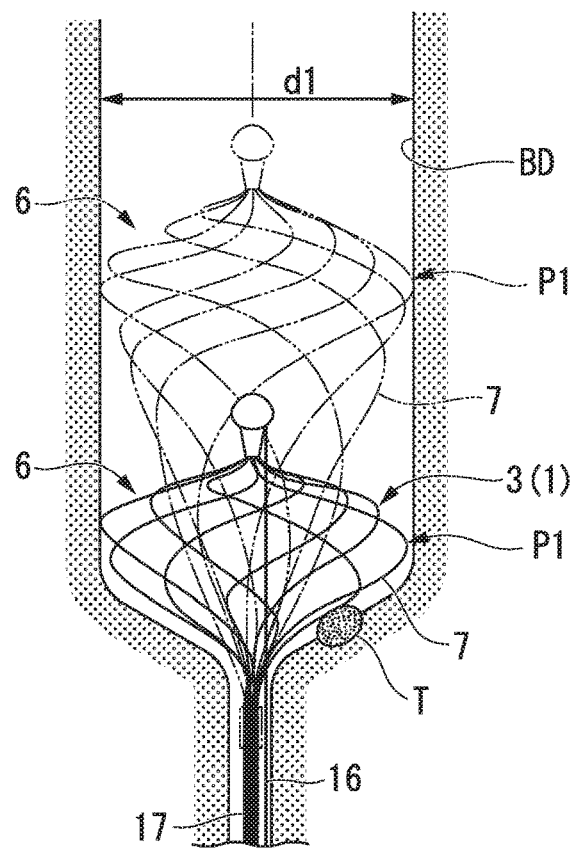
FIG. 8 is a schematic diagram for describing a manipulation of the basket section of the fragmentation tool according to the first embodiment.
Figure 9:
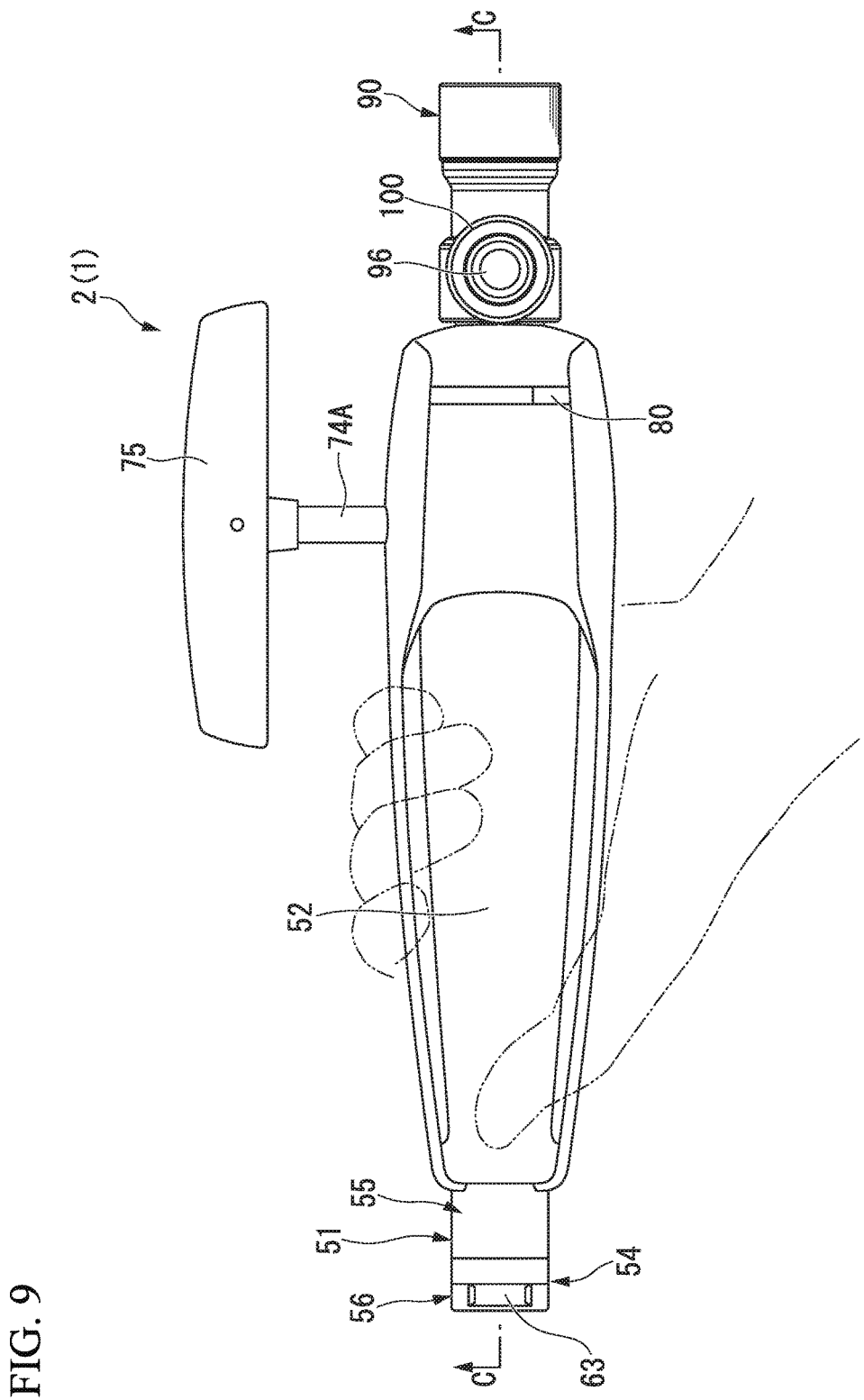
FIG. 9 is a plan view showing a manipulation section of the calculus fragmentation device according to the first embodiment.
Figure 10:
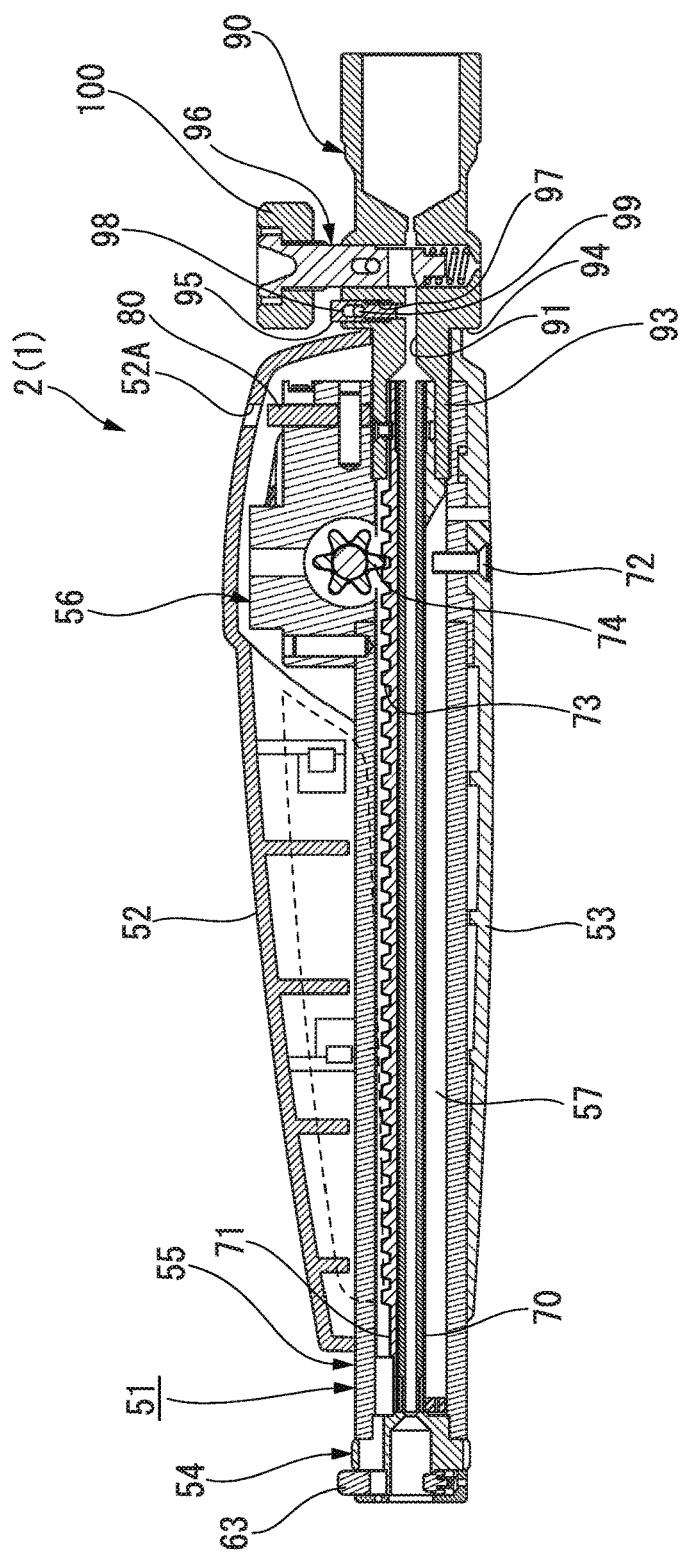
FIG. 10 is a cross-sectional view taken along line C-C of FIG. 9.
Figure 11:
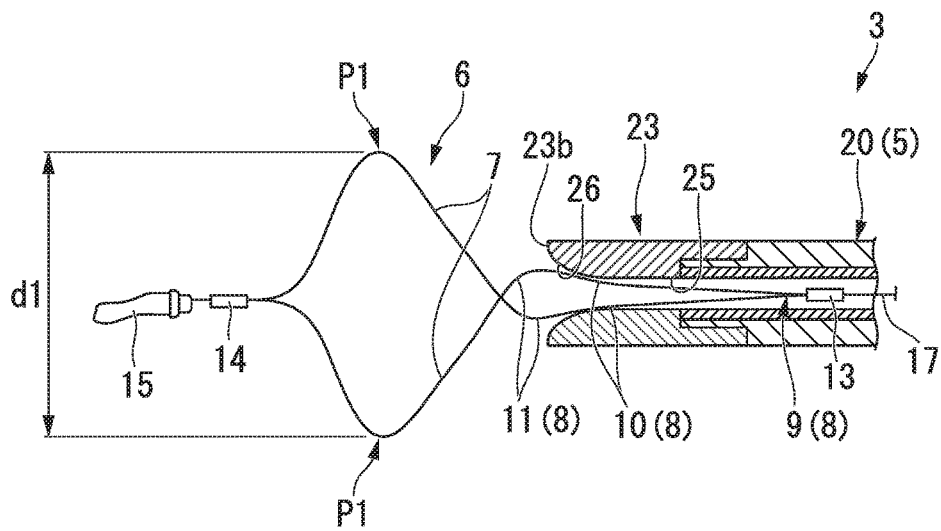
FIG. 11 is a view for describing a function of the calculus fragmentation device of the first embodiment.

A calculus fragmentation device according to a first embodiment of an endoscopic treatment instrument of the present invention will be described. FIG. 1 is a side view showing a fragmentation tool in the calculus fragmentation device of the present embodiment. FIG. 2 is a partial cross-sectional enlarged view showing a configuration of a distal end portion of the fragmentation tool. FIG. 3 is a cross-sectional view taken along line A-A of FIG. 2. FIG. 4 is a cross-sectional view taken along line B-B of FIG. 2. FIG. 5 is a schematic diagram showing a structure of elastic wires provided in a basket section of the fragmentation tool. FIG. 6 is a partial cross-sectional view showing a relationship between shapes of the distal end cover and the elastic wire of the fragmentation tool. FIG. 7 is a schematic diagram for describing a function of the elastic wire. FIG. 8 is a schematic diagram for describing a manipulation of the basket section of the fragmentation tool. FIG. 9 is a plan view showing a manipulation section of the calculus fragmentation device. FIG. 10 is a cross-sectional view taken along line C-C of FIG. 9.

A calculus fragmentation device 1 of the present embodiment shown in FIGS. 1 and 9 is inserted through a treatment tool channel of an endoscope, and is used for a procedure of fragmenting a calculus occurring in luminal tissues such as the bile duct, for example. The calculus fragmentation device 1 has a manipulation section 2 manipulated outside of a body by an operator or the like. A fragmentation tool 3 can be mounted in the manipulation section 2.

As shown in FIGS. 1 and 2, the fragmentation tool 3 has a main body unit 4 which is attachable to or detachable from the manipulation section 2, an elongated and flexible insertion section 5 extending from a distal end of the unit main body 4, and a basket section 6 used as a treatment section to be protruded from or be retracted into a distal end of the insertion section 5.

The basket section 6 is provided for capturing foreign matter T (referring to FIG. 8) such as a calculus in the body and discharging the foreign matter outside of the body. The basket section 6 has a plurality of elastic wires 7 fixed to a distal end of a manipulation wire 17, a first locking section 13 configured to gather the plurality of elastic wires 7 at part of intermediate sections of the elastic wires 7, a second locking section 14 configured to gather the plurality of elastic wires 7 at distal ends of the elastic wires 7, and a center wire 16 extending into the insertion section 5 through an inside of the basket section 6.

The basket section 6 is configured of the elastic wires 7 located between the first locking section 13 and the second locking section 14 in a basket shape as a whole.

Shapes of the elastic wires 7 forming the basket section 6 are not particularly limited and the each of the elastic wires 7 only has to be a spiral shape. Hereinafter, a specific configuration of the elastic wires 7 will be exemplified.

The elastic wires 7 shown in FIGS. 3 to 6 are configured by a single wire or a stranded wire of a highly elastic material such as a super-elastic alloy. The plurality of elastic wires 7 in a basket-like section of the basket section 6 have spiral shapes wound in the same direction as each other. As a material of the elastic wires 7, for example, a nickel titanium alloy can be adopted. As the material of the elastic wires 7, stainless steel, a stainless steel alloy, or the like may be adopted. Although the basket section 6 is configured by eight elastic wires 7 in the present embodiment, the basket section 6 may be configured by a plurality of elastic wires in consideration of ease of capture or difficulty of capture of calculus. The elastic wires 7 of the present embodiment are wires which are single wires with a circular cross section. When the elastic wires 7 are stranded wires, a bundle of strands of the elastic wires 7 seen in the radial cross section of the elastic wires 7 only has to be a substantially circular shape. Cross-sectional shapes of the elastic wires 7 are not particularly limited. For example, the elastic wires 7 may be wires with polygonal cross sections.

The plurality of elastic wires 7 are disposed around a center line O at equal intervals as shown in FIGS. 3 and 4 in which the center line O is used as a linear line connecting a proximal end and a distal end of the basket section 6. A position of the center line O at the basket section 6 substantially coincides with a position of an extension line along which a central axis of the manipulation wire 17 (referring to FIG. 2) extends to a distal side thereof.

The first locking section 13 and the second locking section 14 shown in FIG. 2 are preferably tubular members through which a plurality of elastic wires 7 are inserted. The first locking section 13 and the second locking section 14 are fixed to the plurality of elastic wires 7 through brazing, welding, caulking, resin welding, an adhesive, a combination thereof, or the like. The first locking section 13 and the second locking section 14 are not limited to a configuration in which the tubular members fixed to the elastic wires 7 are provided and a configuration in which the elastic wires 7 are directly fixed to each other may be adopted. The plurality of elastic wires 7 are held by the first locking section 13 and the second locking section 14 to expand into a basket shape with no external force applied. A gap between the elastic wires 7 expanded into a basket shape is a gap for the purpose of taking a foreign matter T as an object to be treated such as calculus inside the basket section 6. Even if gaps of the basket section 6 in an initial state thereof are small, the elastic wires 7 are deformed when a calculus is taken in, a gap that the foreign matter T may enter is created, and thus the calculus can be taken in.

A protective member 15 with a spherical shape or a shape without edges is attached to a distal end of the second locking section 14 for the purpose of preventing the second locking section 14 or the elastic wires 7 from sticking to or catching on biological tissues. The protective member 15 and the second locking section 14 may be made as an integral member.

The center wire 16 functions as a core member configured to hold a shape of the basket section 6. The center wire 16 is made of an elastic member with a linear shape in a state in which an external force is not applied to the elastic member. A distal end of the center wire 16 is fixed to the protective member 15. A proximal end of the center wire 16 is located in the insertion section 5. The proximal end of the center wire 16 is located inside the insertion section 5 even in a state in which the basket section 6 completely projects from the insertion section 5.

The basket section 6 projects from a distal end of the insertion section 5 or is retracted into the insertion section 5 by advancing or retracting the manipulation wire 17 in a central axis direction of the insertion section 5.

When the basket section 6 projects from the insertion section 5, the basket section 6 has a basket shape due to restoring forces of the elastic wires 7.

When the basket section 6 is retracted from an opening of the distal end of the insertion section 5 into the insertion section 5, the elastic wires 7 of the basket section 6 are pressed by an inner surface of the insertion section 5. The elastic wires 7 elastically deform such that the basket section 6 becomes smaller than an inner diameter of the insertion section 5.

As described above, the manipulation wire 17 advances or retracts in a central axis direction of the insertion section 5 such that the basket section 6 is opened or closed in a radial direction orthogonal to a central axis of the manipulation wire 17.

In a state in which an external force is not applied to the basket section 6, a size of the basket section 6 in a radial direction thereof is maximized at a position closer to the second locking section 14 than to an intermediate position between the first locking section 13 and the second locking section 14. A section at which the size of the basket section 6 in the radial direction thereof is maximized is referred to as a maximum diameter section P1 (referring to FIG. 2).

In the present embodiment, an outer diameter d1 of a maximum diameter section P1 may be determined in consideration of shapes of luminal tissues as a place to be treated using the basket section 6. For example, the outer diameter d1 (referring to FIG. 8) of the maximum diameter section P1 suitable for removing a gallstone is set to a size in which the plurality of elastic wires 7 come into contact with a tube wall of a bile duct BD over the entire circumference thereof. When the calculus fragmentation device 1 is used with respect to luminal tissues other than the bile duct, the outer diameter d1 of the maximum diameter section P1 is appropriately set on the basis of inner diameters of the luminal tissues as a target.

The elastic wires 7 of the basket section 6 are formed in a spiral shape in which a winding pitch (an amount by which the elastic wires 7 advance to the second locking section 14 side when they advance by a predetermined angle in a circumferential direction along spirals of the elastic wires 7) gradually decreases as the elastic wires 7 go from the distal end of the manipulation wire 17 to the second locking section 14. In the present embodiment, the elastic wires 7 are wound in a range of about 225° between the first locking section 13 and the second locking section 14 in the circumferential direction. Furthermore, angles wound in the circumferential direction depending on slopes of the elastic wires 7 are appropriately set.

In a state in which an external force is not applied to the basket section 6, as shown in FIG. 2, tangents of every of the plurality of elastic wires 7 at the maximum diameter section P1 are inclined at an angle at which an angle θ formed with respect to a plane of the maximum diameter section P1 orthogonal to the center line O is 45° or less. The elastic wires 7 at a proximal end side are formed in a shape that is directed to an axial direction, while the elastic wires 7 toward the maximum diameter section are formed in a shape that drops down sideways with respect to the plane orthogonal to the center line O, and the elastic wires 7 at a distal end side are formed to be wound in a circumferential direction thereof.

In a state in which proximal end portions of the elastic wires 7 are arranged inside the insertion section 5, a basket shape of the basket section 6 configured by the elastic wires 7 is smaller than that in a case in which the elastic wires 7 are outside of the insertion section 5. As shown in FIG. 7, a distance from the center line O to the maximum diameter section P1 when viewed from a center line O direction of the basket section 6 is substantially maintained to be substantially unchanged between a state before the elastic wires 7 move into the insertion section 5 (which are shown by a chain double dashed line in FIG. 7) and a state after the elastic wires 7 have moved into the insertion section 5 (which are shown by a solid line in FIG. 7), and to be substantially equal to a radius d2 which is half of an external size d1 of the maximum diameter section P1.

The basket section 6 of the present embodiment can be maintained to have a substantially constant external size d1 in luminal tissues such as, for example, the bile duct BD (referring to FIG. 8) regardless of a degree of drawing of the basket section 6 with respect to the insertion section 5.

The elastic wires 7 have a three-dimensional complex shape and have inflection points when shown in a projective view.

In a projection direction shown in FIGS. 5 and 6, curved sections 8 (a first curved section 9, a second curved section 10, and a third curved section 11) with different radii of curvature are provided in a region between proximal end portions 7b of the elastic wires 7 and the maximum diameter section P1. The first curved section 9, the second curved section 10, and the third curved section 11 are arranged in such an order in a region along the elastic wires 7 from the proximal end portions 7b of the elastic wires 7 toward the maximum diameter section P1. The radii of curvature (a radius of curvature R1 of the first curved section 9, a radius of curvature R2 of the second curved section 10, and a radius of curvature R3 of the third curved section 11) of the three curved sections 8 between the proximal end portions 7b of the elastic wire 7 and the maximum diameter section P1 are larger than a radius of curvature R0 which will be described later of a curved surface 26 of a distal end cover 23 which will be described later at all times.

A folded angle of the elastic wires 7 folded from the second locking section 14 is preferably to be equal to or more than 60°. An expansion force of the basket section 6 is easily maintained when the folded angle is closer to 90°. If the angle of the elastic wires 7 is closer to 90°, an amount of basket opening and closing force is larger. The folded angle is appropriately set in consideration of the amount of basket opening and closing force. If the elastic wires 7 are folded at a position in the immediate vicinity of the second locking section 14, a folded load is applied to the elastic wires and thus the elastic wires may be easily broken or an amount of basket opening and closing force is larger. The elastic wires 7 of a section fixed to the second locking section 14 may have a gentle round shape, a plurality of folded sections, a linear section, or the like.

As shown in FIG. 2, part of the basket section 6 closer to a proximal side than to the maximum diameter section P1 is a capture section P2 configured to take in the foreign matter T such as calculus. Part of the basket section 6 more distal than the maximum diameter section P1 is configured such that a winding pitch of the elastic wires 7 is small and gaps between the elastic wires 7 are small and functions as a capture section P3 out of which it is hard for a calculus captured inside the basket section 6 to slip out.

As shown in FIG. 2, the insertion section 5 has a coil sheath 20 as a first sheath section, a tube sheath 21 arranged as a second sheath section inside the coil sheath 20, and the annular distal end cover 23 provided at an opening of a distal end of the coil sheath 20.

The coil sheath 20 is manufactured by tightly winding a metallic flat plate. The distal end cover 23 is fixed to a distal end portion of the coil sheath 20 using brazing, laser welding, or the like. The coil sheath 20 has a strength to withstand an amount of force applied to the calculus fragmentation device 1 in a manipulation of fragmenting calculus and has flexibility in which it can be bent along a channel of the endoscope. In other words, the coil sheath 20 has a strength in which it hardly buckles with respect to a compressive force in a center line direction of the coil sheath 20 itself and can be deformed in a direction in which a center line of the coil sheath 20 itself is bent.

The distal end cover 23 shown in FIGS. 2 and 6 is annular and made of metal. The distal end cover 23 is arranged to be coaxial with the coil sheath 20, is fixed to the coil sheath 20, and communicates with the coil sheath 20.

The distal end cover 23 has a first opening 23a which is open toward the coil sheath 20, a second opening 23b which is open toward an opposite side to the first opening 23a, and a passage 24 configured to connect the first opening 23a and the second opening 23b.

The passage 24 has an inner peripheral surface 25 connected to a first opening and the curved surface 26 configured to connect an inner peripheral surface and a second opening.

The elastic wires 7 of the basket section 6 are able to come into contact with the inner peripheral surface 25 of the passage 24. The inner peripheral surface 25 of the passage 24 comes into contact with the elastic wires 7 so that the inner peripheral surface 25 holds the basket section 6 in a state in which the elastic wires 7 are elastically deformed. When the calculus fragmentation device 1 of the present embodiment is used, a shape of the basket section 6 projecting from or retracted into the distal end of the insertion section 5 is mainly regulated by the passage 24.

The curved surface 26 of the passage 24 is bent to have a radius of curvature R0 larger than a wall thickness t (which is a distance between an outer peripheral surface 27 and the inner peripheral surface 25 of the distal end cover when viewed from a center line X1 direction of the distal end cover 23 in the present embodiment) of the distal end cover 23 at a cross section including a center line X1 of the distal end cover 23. The curved surface 26 of the passage 24 is bent such that an inner diameter of the distal end cover 23 gradually increases as it goes from the curved surface 26 toward the second opening 23b. The curved surface 26 is a surface along which the elastic wires 7 can slide in a process in which the elastic wires 7 of the basket section 6 are protruded from or retracted into the insertion section 5. The curved surface 26 of the passage 24 is bent to be slightly convex toward a direction of the center line X1 direction of the distal end cover 23, as compared with a known tapered surface having a conical lateral surface. The curved surface 26 is configured to have a smooth surface.

A shape of the curved surface 26 is defined in accordance with a shape of the elastic wires 7 of the basket section 6. For example, the radius of curvature R0 of the curved surface 26 in a cross section including the center line X1 of the distal end cover 23 is smaller than any of three radii of curvature of the curved sections 8 (the radius of curvature R1 of the first curved section 9, the radius of curvature R2 of the second curved section 10, and the radius of curvature R3 of the third curved section 11) provided between the proximal end portions 7b of the elastic wires 7 and the maximum diameter section P1. Since the curved surface 26 is a curved surface having no corners or protrusions coming into contact with the elastic wires 7, sliding resistance with respect to the elastic wires 7 is difficult to occur.

The tube sheath 21 is formed by a resinous tube. The manipulation wire 17 is inserted through the tube sheath 21 to be freely advanceable and retractable. The tube sheath 21 is inserted between the metallic coil sheath 20 and the metallic manipulation wire 17 such that the basket section 6 and the manipulation wire 17 are easily rotated around an axis and the basket section 6 is easily opened or closed.

The unit main body 4 shown in FIG. 1 has a substantially cylindrical main body 30, a substantially tubular fixing section 31 fixed to the coil sheath 20 and the tube sheath 21, and an engagement section 40 configured to engage the fragmentation tool 3 with the manipulation section 2.

An insertion hole 35 through which the manipulation wire 17 is inserted is formed in a main body 30. A tubular mouthpiece 37 which is open in an outer peripheral portion of the main body 30 is screwed into the intermediate part of the insertion hole 35. For example, when a syringe filled with a contrast medium is mounted in the mouthpiece 37 and the contrast medium is pushed out from the syringe, the contrast medium can be injected from the mouthpiece 37 into a body through the distal end of the insertion section 5 via the insertion hole 35. The main body 30 has a liquid-tight structure between the inner surface of the insertion hole 35 and the manipulation wire 17 such that the contrast medium or the like does not flow toward a proximal end side (a side at which the engagement section 40 is arranged) of the insertion hole 35.

The manipulation wire 17 is inserted and extended through the unit main body 4 by being inserted through the insertion hole 35 formed in the main body 30 of the unit main body 4. The manipulation wire 17 is inserted through the tube sheath 21. A reduced diameter section 41 is formed is a proximal end of the manipulation wire 17. The proximal end of the manipulation wire 17 is connected to the manipulation section 2 such that the manipulation wire 17 can advance or retract through a manipulation which will be described later in the manipulation section 2.

Next, a manipulation section 2 mounted in the fragmentation tool 3 will be described with reference to FIGS. 9 and 10. Descriptions of the manipulation section as the following is an example of a manipulation section which can suitably operate the fragmentation tool 3 and the present invention is not limited thereto.

The manipulation section 2 shown in FIGS. 9 and 10 has a manipulation section main body 51 in which the fragmentation tool 3 is inserted from a distal end side thereof and mounted. A proximal end side of the manipulation section main body 51 is screwed such that covers 52 and 53 vertically surround the manipulation section main body 51. The manipulation section main body 51 has a sheath connecting section 54, a tubular guide section 55, a main body 56 screwed to a proximal end portion of the guide section 55, a guide hole 57 configured to pass through the guide section 55 and the main body 56 in an axial direction thereof, and a gripping section 90 which can be protruded through or retracted along the guide hole 57 arranged in this order from a distal end side thereof.

The sheath connecting section 54 can accommodate the engagement section 40 of the fragmentation tool 3. The sheath connecting section 54 can connect the unit main body 4 of the fragmentation tool 3 such that the unit main body 4 can be attached to or detached from the manipulation section 2. The sheath connecting section 54 has a sheath connecting button 63 configured to switch a state of engagement with the unit main body 4 of the fragmentation tool 3. In a state in which an operator presses the sheath connecting button 63, the engagement section 40 of the fragmentation tool 3 is attachable to or detachable from the sheath connecting section 54. When the pressing of the sheath connecting button 63 by the operator is released, the sheath connecting section 54 is engaged with the engagement section 40 of the fragmentation tool 3.

A guide tube 70 is fixed to a proximal end of the sheath connecting section 54. The guide tube 70 extends in the guide hole 57 of the manipulation section main body 51 such that these are coaxial with each other. A rack body 71 is mounted in the guide tube 70 to cover an outer circumference of the guide tube 70.

The rack body 71 is supported at an inner circumference side of each of the guide section 55 and the main body 56 to be advanceable and retractable. Rotation of the rack body 71 around an axis thereof is prevented by a screw 72 screwed from the cover 52 side. The rack body 71 is advanceable and retractable in an axial direction of the rack body 71. A rack 73 is formed in the rack body 71 with a predetermined length in the axial direction thereof. A pinion 74 engaged with the rack 73 is rotatably supported by a bearing fixed to the main body 56.

A shaft 74A of the pinion 74 extends toward an outside of the cover 53. A handle 75 is fixed to an end portion of the shaft 74A. In the case of the shaft 74A of the pinion 74, rotation in only one predetermined direction designated by a changeover switch 80 and free rotation can be selected through a known ratchet structure.

The handle 75 is a member which is rotatably operated by the operator in order to transmit a force for fragmenting calculus or the like to the manipulation wire 17. Although details will be described as the following, in the present embodiment, the handle 75 is rotated in a predetermined direction to apply a traction force to the basket 6 via the manipulation wire 17 to fragment the calculus, in a state in which the distal end cover 23 fixed to the coil sheath 20 supports the calculus. The handle 75 has a flat shape. For this reason, the operator may easily grasp the handle 75 and easily applies an amount of force to the handle 75.

A distal end portion 93 of the gripping section 90 can be inserted into the guide hole 57 on the manipulation section main body 51 side of the manipulation section 2. A hole 91 which is open in the distal end portion 93 is formed to communicate with a hole in the guide tube 70. In the gripping section 90, a diameter of an abutting surface 94 which can abut the covers 52 and 53 increases when the abutting surface 94 is formed in the middle of the gripping section 90 from the distal end portion 93 toward a proximal end thereof An insertion hole 97 through which an outer peripheral portion of the gripping section 90 communicates with the hole 91 inside the gripping section 90 is formed to penetrate through an increased diameter section of the gripping section 90 to be orthogonal to an axis thereof. A pin 95 used as a second engagement member is inserted into the insertion hole 97. A long hole 98 is formed in the pin 95. A lock pin 99 is inserted into the long hole 98 so that the pin 95 is prevented from falling out of the insertion hole 97. In a state in which the pin 95 is most deeply inserted into the insertion hole 97, a distal end portion of the pin 95 projects into the hole 91.

A wire connecting button 96 used as a first engagement member and a stopper 100 configured to restrict a stroke in a direction along which the wire connecting button 96 is pushed to the gripping section 90 are provided more proximal than the insertion hole 97.

When the wire connecting button 96 is moved in the direction along which the wire connecting button 96 is pushed to the gripping section 90, the manipulation wire 17 can be attachable to or detachable from the manipulation section 2. When a force used to move the wire connecting button 96 in the direction along which the wire connecting button 96 is pushed to the gripping section 90 is released, the wire connecting button 96 returns to the original position in a direction in which it moves away from the gripping section 90 and connects the manipulation wire 17 to the manipulation section 2.

Next, a function of the calculus fragmentation device 1 will be described focusing on a manipulation principle of the basket section 6. FIGS. 11 to 15 are views for describing a function of the calculus fragmentation device. Although the manipulation principle of the basket section 6 in which the plurality of elastic wires 7 of the present embodiment are provided will be shown below, a configuration and an operation of the basket section 6 are not limited to the following configuration and operation.

As shown in the FIG. 8, the basket section 6 is guided into, for example, luminal tissues such as the bile duct BD by using the endoscope. Subsequently, the basket section 6 projects from the insertion section 5 to take in calculus or the like inside the basket section 6 (referring to FIG. 1). When the basket section 6 projects from the insertion section 5, a basket-like shape of the basket section 6 is restored in the luminal tissues due to a restoring force of the elastic wires 7 as shown in FIG. 8. The elastic wires 7 in the basket section 6 with the basket-like shape come into contact with an inner surface of the luminal tissues, are pushed back by the luminal tissues, and thus are elastically deformed. Thus, the elastic wires 7 come in close contact with the luminal tissues. In the present embodiment, the maximum diameter section P1 of the basket section 6 is pressed against the inner surface of the luminal tissues.

Figure 12:
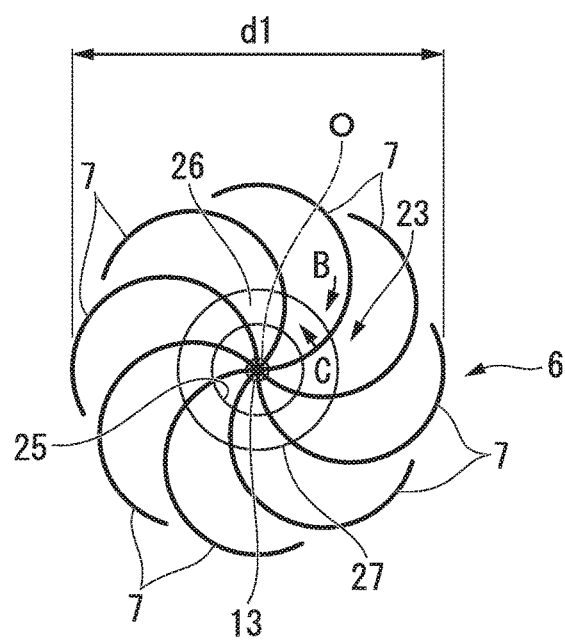
FIG. 12 is a view for describing a function of the calculus fragmentation device according to the first embodiment.
Figure 13:
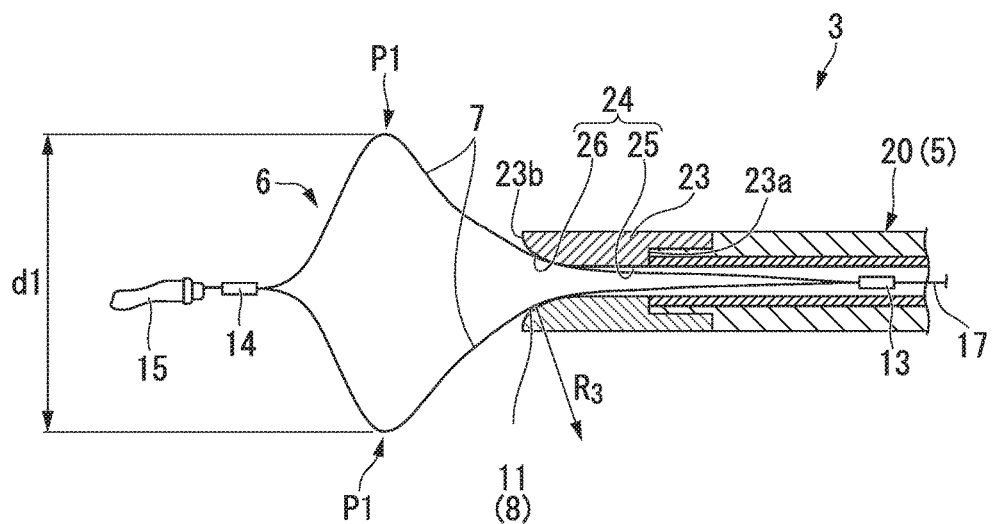
FIG. 13 is a view for describing a function of the calculus fragmentation device according to the first embodiment.
Figure 14:
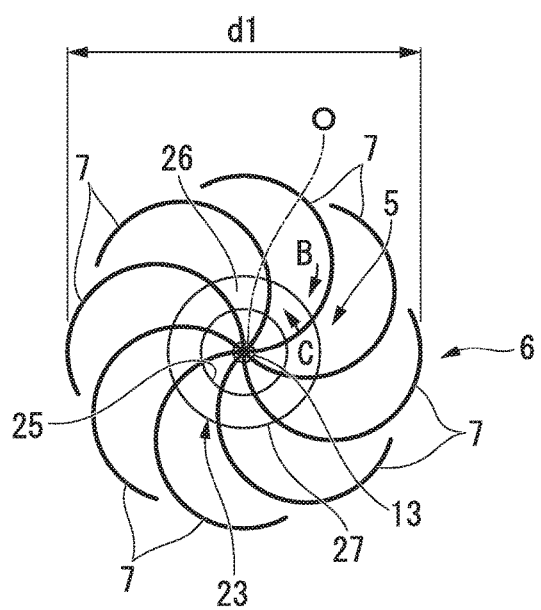
FIG. 14 is a view for describing a function of the calculus fragmentation device according to the first embodiment.
Figure 15:
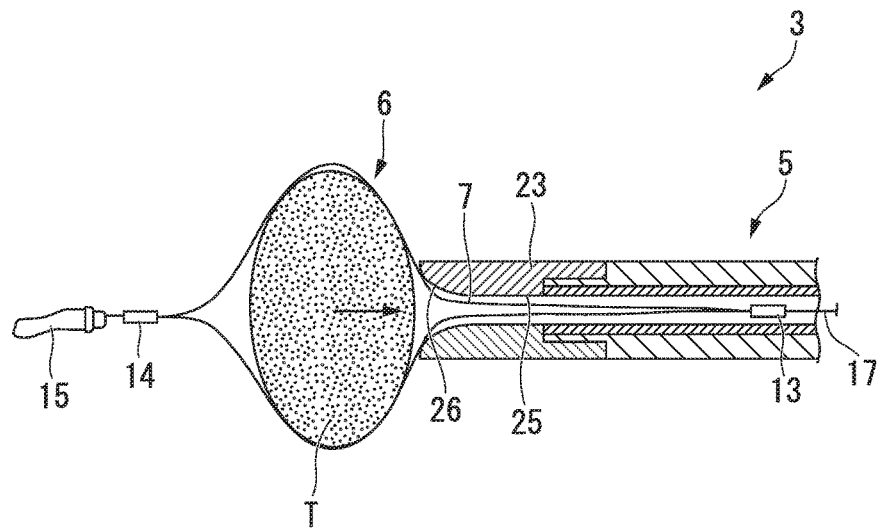
FIG. 15 is a view for describing a function of the calculus fragmentation device according to the first embodiment.

For example, after calculus or the like is taken inside the basket section 6, the basket section 6 is retracted into the coil sheath 20 such that the basket shape of the basket section 6 becomes smaller and the calculus or the like is captured in the capture section P3 of the basket section 6. As schematically shown in FIGS. 11 to 14, the elastic wires 7 of the basket section 6 gradually move from the first locking section 13 side into the coil sheath 20 in a process in which the basket section 6 is retracted into the coil sheath 20. Until the third curved section 11 reaches the vicinity of the distal end cover 23 in the process in which the basket section 6 is retracted into the coil sheath 20, as shown in FIGS. 12 and 14, the external size d1 of the basket section 6 does not substantially change.

Since each of the plurality of elastic wires 7 has a restoring force which restores itself to a predetermined initial shape such that the basket section 6 restores to a basket shape, the plurality of elastic wires 7 are pressed against the inner peripheral surface 25 and the curved surface 26 of the distal end cover 23 arranged on the distal end of the coil sheath 20. The plurality of elastic wires 7 are retracted into the coil sheath 20 while sliding with respect to the curved surface 26 and the inner peripheral surface 25 of the distal end cover 23. Since the plurality of elastic wires 7 form a spiral shape, contact positions between the plurality of elastic wires 7 and the curved surface 26 move in a circumferential direction of the distal end cover 23 in accordance with the drawing-in operation of the elastic wires 7 into the coil sheath 20 (referring to FIG. 12). Such movement is caused due to a change in relative positions in the retraction operation occurring when the plurality of elastic wires 7 form a spiral shape rather than rotation of the basket section 6 itself.

In the present embodiment, since the elastic wires 7 are circular cross-sectional wires and the curved surface 26 is provided on an inner surface at a distal end side of the distal end cover 23, outer surfaces of the elastic wires 7 come in point contact with the curved surface 26. In the present embodiment, the curved surface 26 is a smooth surface. Thus, sliding resistance on the elastic wires 7 with respect to the curved surface 26 is small.

As described above, in the calculus fragmentation device 1 of the present embodiment, since the curved surface 26 at the distal end side of the distal end cover 23 coming into contact with the plurality of elastic wires 7 is provided to have a bent shape over the entire circumference, situations such as that the plurality of elastic wires 7 are caught on the curved surface 26 or the curved surface 26 causes sliding resistance with respect to the elastic wires 7 will not occur.

As a result, resistance when the plurality of elastic wires 7 are retracted into the coil sheath 20 is small, and thus the basket section 6 having the plurality of elastic wires 7 can be easily retracted into the coil sheath 20.

In the present embodiment, the curved surface 26 is a series of continuous annular surfaces in the circumferential direction of the distal end cover 23. The plurality of elastic wires 7 can easily move in the circumferential direction of the distal end cover 23 in contact with the curved surface 26. As a result, since the basket section 6 having the elastic wires 7 with a spiral shape can slide above the curved surface 26 without being caught with respect to the distal end cover 23, a force applied for fragmenting calculus is suitably transmitted to the calculus via the elastic wires 7 and thus the calculus can be easily fragmented.

(Second Embodiment)

Figure 16:
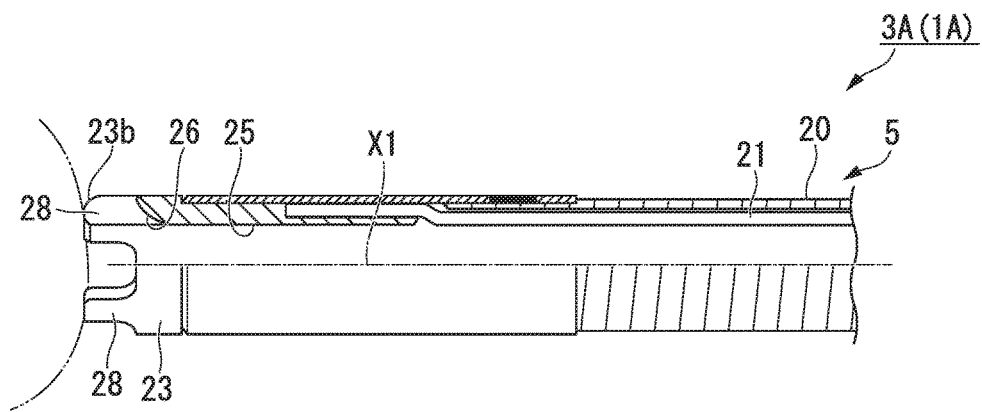
FIG. 16 is a partial cross-sectional side view showing a fragmentation tool of a calculus fragmentation device according to a second embodiment of the present invention.
Figure 17:
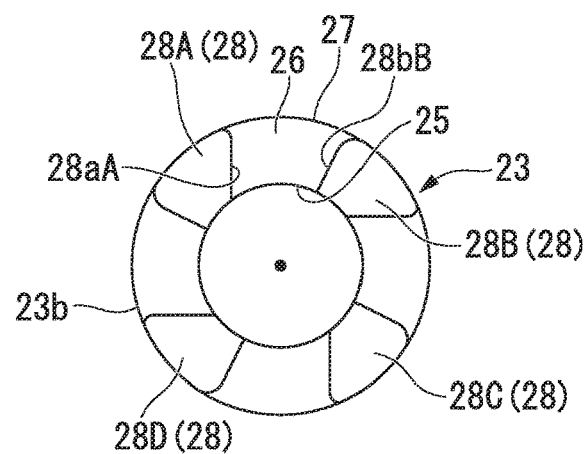
FIG. 17 is a front view of the fragmentation tool according to the second embodiment.
Figure 18:
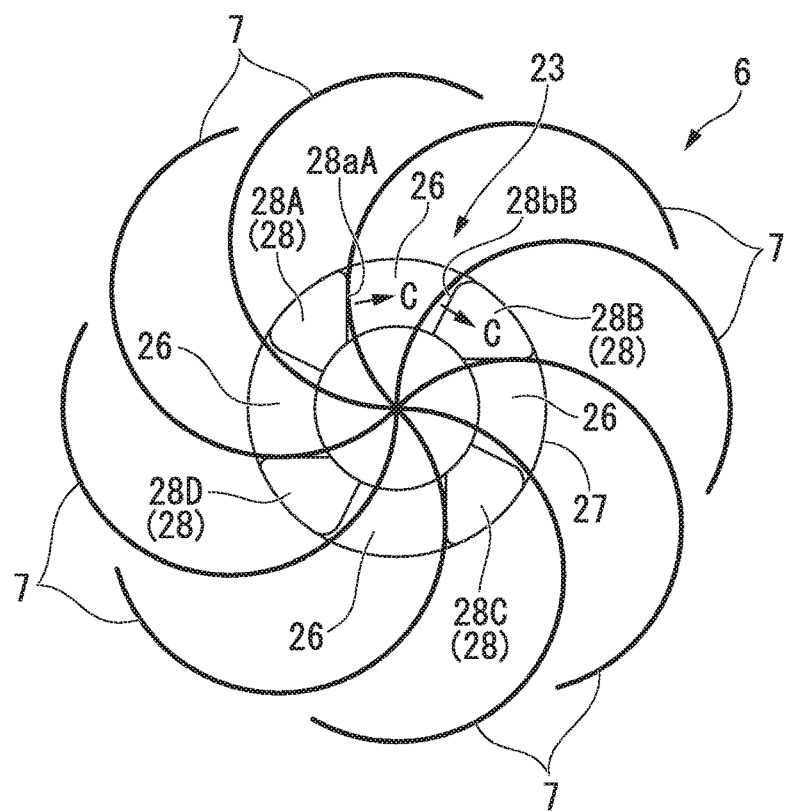
FIG. 18 is a schematic diagram for describing a positional relationship between a distal end cover and elastic wires of the fragmentation tool according to the second embodiment.

A second embodiment of the present invention will be described. FIG. 16 is a partial cross-sectional side view showing a fragmentation tool of a calculus fragmentation device of the second embodiment of the present invention. FIG. 17 is a front view of the fragmentation tool. FIG. 18 is a schematic diagram for describing a positional relationship between a distal end cover and elastic wires of the fragmentation tool.

A calculus fragmentation device 1A of the present embodiment shown in FIGS. 16 to 18 has a fragmentation tool 3A with a configuration different from that of the fragmentation tool 3 disclosed in the first embodiment. The calculus fragmentation device 1A can be attached to the manipulation section 2 disclosed in the first embodiment and used.

As shown in FIG. 16, a configuration of the fragmentation tool 3A and a configuration of the fragmentation tool 3 disclosed in the first embodiment differ in a point that the fragmentation tool 3A has a plurality of projections 28 extending in a direction parallel to the center line X1 of a distal end cover 23 on the distal end cover 23 disclosed in the first embodiment.

As shown in FIGS. 16 and 17, the plurality of the projections 28 are provided apart from each other in a circumferential direction of the distal end cover 23 at a second opening 23b of the distal end cover 23.

As shown in FIG. 18, a gap configured to allow at least one elastic wire 7 to enter is provided between two neighboring projections (for example, a first projection 28A and a second projection 28B) among the plurality of projections 28. In the present embodiment, four projections 28 (the first projection 28A, the second projection 28B, a third projection 28C, and a fourth projection 28D) are evenly arranged in the circumferential direction of the distal end cover 23.

The plurality of projections 28 are formed to correspond to the number of elastic wires 7. For example, an integer multiple of the number of projections 28 coincides with the number of elastic wires 7. In the present embodiment, the four projections 28 correspond to eight elastic wires 7 and two of the elastic wires 7 enter gaps (hereinafter referred to as "groove sections") formed between the four projections 28.

When calculus is fragmented in the present embodiment, the elastic wires 7 enter the groove sections between the four projections 28 such that a tightening force at the manipulation section 2 side is applied to the elastic wires 7 via an insertion section 5. As shown in FIG. 16, projection ends in each of the plurality of projections 28 support calculus T and the elastic wires 7 are inserted to be advanceable from or retract into the groove sections, such that the elastic wires 7 are not surrounded by the calculus T and the distal end cover 23, and thus the elastic wires 7 can move smoothly.

As shown in FIGS. 16 and 17, in the present embodiment, the curved surface 26 disclosed in the first embodiment is provided in the groove sections between the four projections 28.

As shown in FIG. 18, a first lateral surface 28aA of the first projection 28A directed toward the second projection 28B and a second lateral surface 28bB of the second projection 28B directed toward the first projection 28A have bent shapes extending substantially along shapes of the elastic wires 7 with a spiral shape. For example, in the first lateral surface 28aA and the second lateral surface 28bB described above, gaps closer to an outer circumference side of the distal end cover 23 are wider than an inner circumference side of the distal end cover 23 and extend in spiral directions of the elastic wires 7.

As in a relationship between the first lateral surface 28aA and the second lateral surface 28bB which substantially face each other, also with regard to the second projection 28B and the third projection 28C, the third projection 28C and the fourth projection 28D, and the fourth projection 28D and the first projection 28A, in first lateral surfaces and second lateral surfaces, a relationship in which gaps closer to an inner circumference side of the distal end cover 23 than to an outer circumference side of the distal end cover 23 are wider and extend in the spiral directions of the elastic wires 7 is satisfied.

A function of the calculus fragmentation device 1A of the present embodiment will be described. FIGS. 19 to 24 are views for describing a function of the calculus fragmentation device of the present embodiment.

Figure 19:
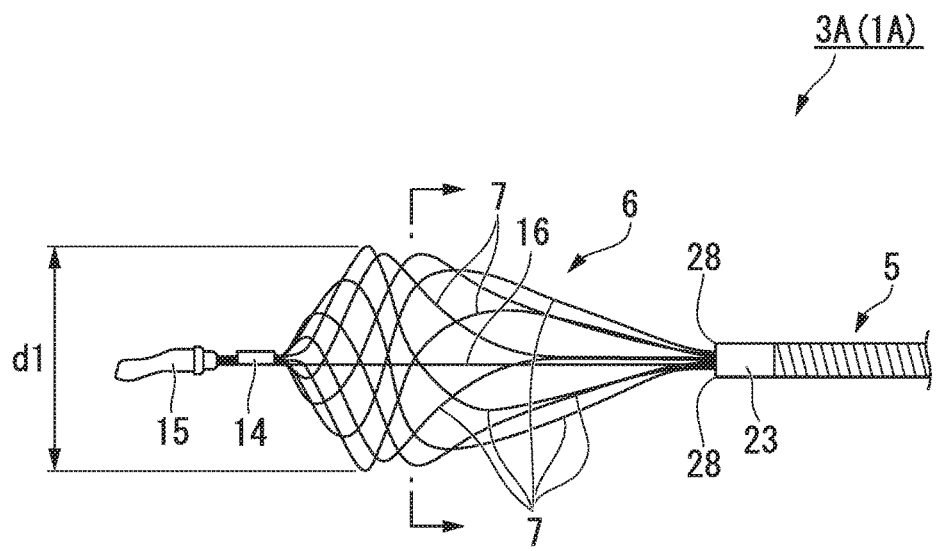
FIG. 19 is a view for describing a function of the calculus fragmentation device of the second embodiment.
Figure 20:
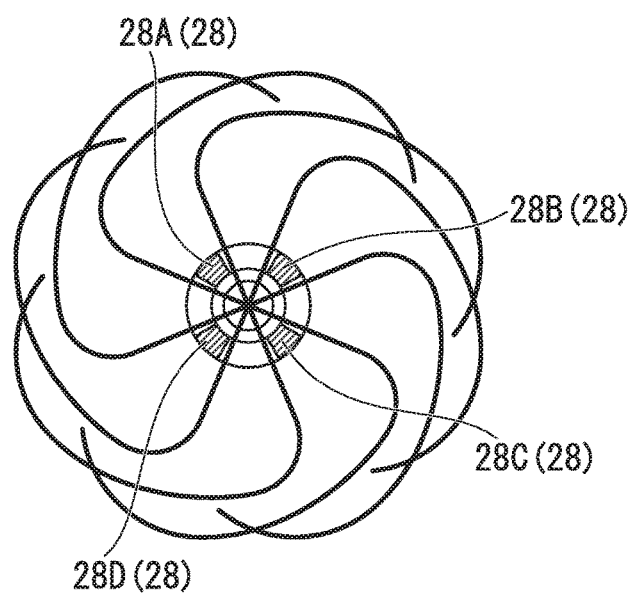
FIG. 20 is a view for describing a function of the calculus fragmentation device according to the second embodiment.

In the calculus fragmentation device 1A of the present embodiment, when the basket section 6 which has been fully protruded from the insertion section 5 starts to be retracted into the insertion section 5, first, as shown in FIGS. 19 and 20, the elastic wires 7 enter the gaps between the plurality of projections 28. In the present embodiment, two elastic wires 7 enter between the neighboring projections 28.

Figure 21:
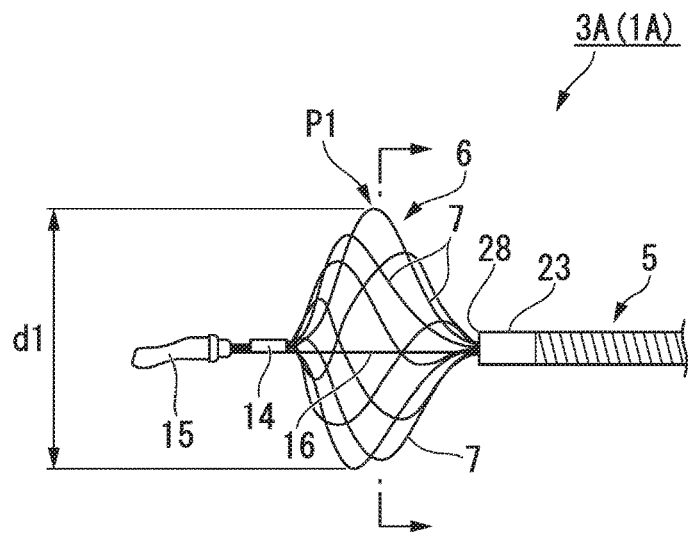
FIG. 21 is a view for describing a function of the calculus fragmentation device according to the second embodiment.
Figure 22:
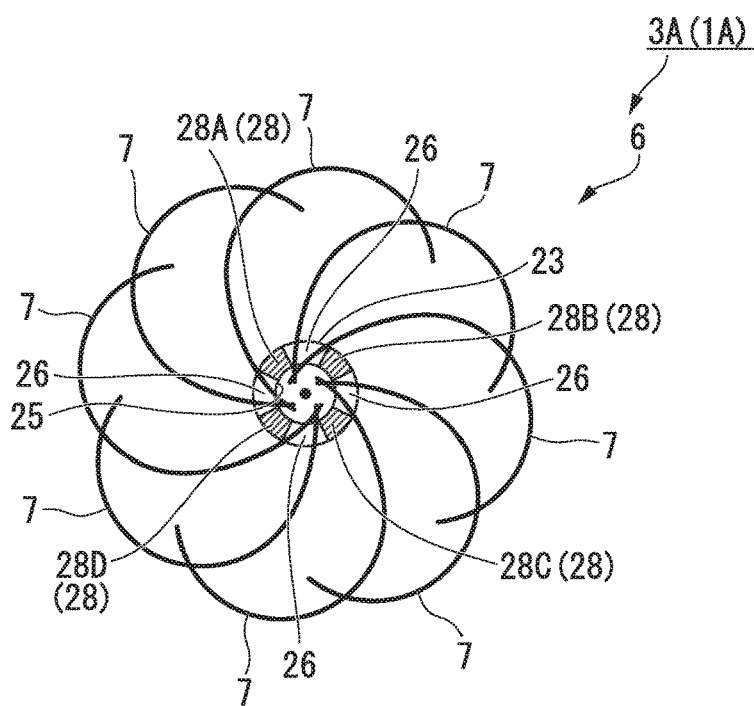
FIG. 22 is a view for describing a function of the calculus fragmentation device according to the second embodiment.

As shown in FIGS. 21 and 22, if the basket section 6 is further retracted into the insertion section 5, as in the first embodiment, an external size of the maximum diameter section P1 is maintained to be substantially equal to an external size d1 before the basket section 6 is retracted.

Also, also in the present embodiment, as in the above-described first embodiment, the elastic wires 7 can easily slide with respect to the curved surface 26. In the present embodiment, the elastic wires 7 enter the groove sections used as the gaps between the projections 28 such that a change in contact positions of the distal end cover 23 with respect to the curved surface 26 and the elastic wires 7 in the circumferential direction thereof is restricted at positions at which the elastic wires 7 abut the projections 28 (referring to FIG. 22). As shown in FIG. 18, the projections 28 of the present embodiment may have the first lateral surface 28aA and the second lateral surface 28bB corresponding to the spiral directions of the elastic wires 7 and sliding resistance may be set to be in a low state without there being catching with respect to an outer surface of the projections 28 even if the elastic wires 7 come into contact with the projections 28.

Figure 23:
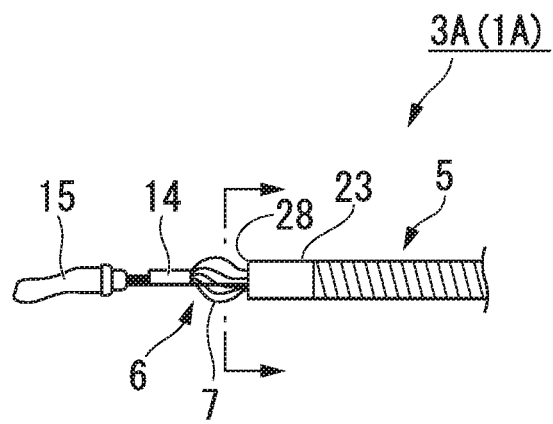
FIG. 23 is a view for describing a function of the calculus fragmentation device.
Figure 24:
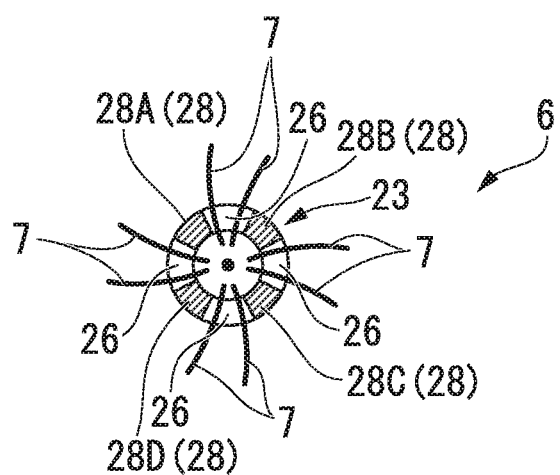
FIG. 24 is a view for describing a function of the calculus fragmentation device according to the second embodiment.

As shown in FIGS. 23 and 24, in a state in which the basket section 6 is further retracted into the insertion section 5 and the second locking section 14 is close to the projections 28, the spiral shape of the elastic wires 7 are almost released and the elastic wires 7 have shapes close to simple bent shape. Thereafter, the basket section 6 is further retracted into the insertion section 5 such that the basket section 6 can be fully accommodated in the insertion section 5.

In the present embodiment, the groove sections formed between the neighboring projections 28 are passages through which the elastic wires 7 freely advance or retract. In addition, the passages form spaces through which the elastic wires 7 freely advance or retract also in a state in which the calculus T abuts the projection ends of the projections 28 (referring to FIG. 16). As a result, since an amount of force by which a handle 75 is rotated to fragment calculus is suitably transferred to the calculus via the elastic wires 7, the calculus can be fragmented using a force lighter than that of when the projections 28 are not provided.

Although the embodiments of the present invention have been described in detail above with reference to the drawings, specific configurations are not limited to such embodiments and also include modifications in design or the like without departing from the gist of the present invention.

Figure 25:
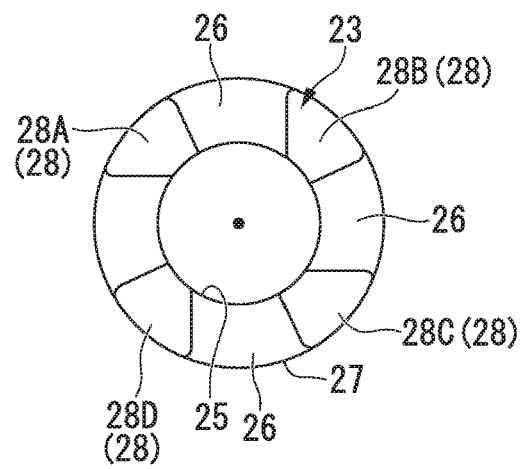
FIG. 25 is a front view illustrating another configuration example of the fragmentation tool of the second embodiment.
Figure 26:
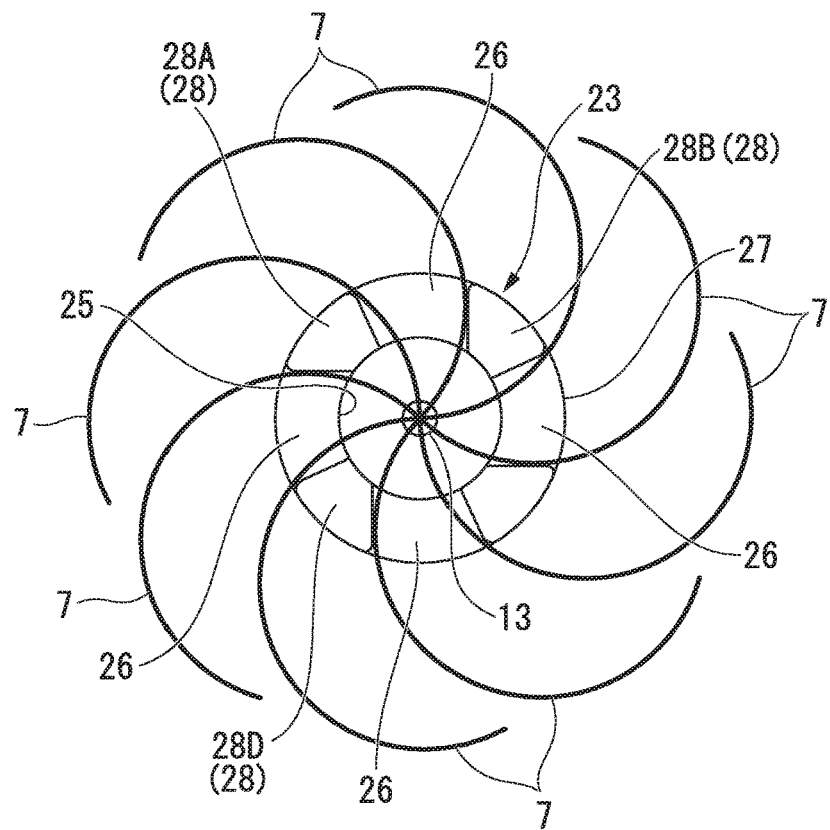
FIG. 26 is a schematic diagram for describing a positional relationship between a distal end cover and elastic wires in the configuration example.

For example, a distal end cover having a projection with a different shape may be provided in a coil sheath to correspond to a spiral basket section in which a winding direction of the elastic wires is reversed as shown in FIGS. 25 and 26 instead of the distal end cover disclosed in the above-described second embodiment.

Figure 27:
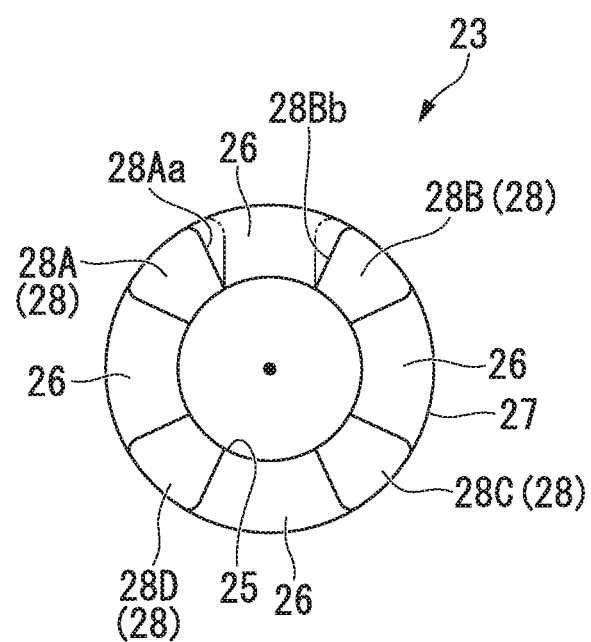
FIG. 27 is a front view illustrating yet another configuration example of the fragmentation tool of the present embodiment.

Also, in the above-described second embodiment, as shown in FIG. 27, the first lateral surface and the second lateral surface which face each other on neighboring projections may be set to have bent shapes in which the first lateral surface (which is indicated by, for example, a reference numeral 28aA) and the second lateral surface (which is indicated by, for example, a reference numeral 28bB) are symmetrical with respect to each other to suitably correspond to both of a basket section having elastic wires with a spiral shape wound in one predetermined direction and a basket section having elastic wires with a spiral shape wound in an opposite direction to such one predetermined direction.

In the above-described second embodiment, a shape of the curved surface between the projections of the distal end cover is not limited. Furthermore, a surface between the projections of the distal end cover may not be a curved surface.

Also, configuration elements represented in the above-described embodiments can be configured through appropriate combinations.

Modifications in design or the like with respect to the above-described specific configurations are not limited to the above-described matters.

In addition, a configuration can be adopted by appropriately combining the configuration elements described in the respective embodiments and the respective modification examples with each other. The present invention is not limited by the above description, and is limited by only appended claims.

What is claimed is:

1. An endoscopic treatment instrument comprising:
    a sheath configured to be inserted through a channel of an endoscope, the sheath having proximal and distal ends and a longitudinal axis;
    a basket section configured to be protruded from and retracted into the distal end of the sheath, and is formed by a plurality of elastic wires with a spiral shape wound in a same direction; and
    a manipulation wire connected to the basket section and inserted through the sheath to be advanceable and retractable with respect to the sheath between an advanced position in which the basket section protrudes from the distal end of the sheath and a retracted position in which the basket section is received in the sheath; wherein:

the sheath includes, in seriatim, from the proximal end to the distal end:
- a tubular section having a constant inner diameter and inner circumference and a center axis, the center axis being along the longitudinal axis of the sheath, the tubular section configured to receive the basket section when the manipulation wire is in the retracted position; and
- a curved surface section having (1) proximal and distal ends and (2) an inner surface with (a) a circular cross section and (b) a diameter at the proximal end of the curved surface section which is the same as the inner diameter of the tubular section, the diameter of the inner surface increasing along a curve from the proximal end of the curved surface section to the distal end of the curved surface section;

each of the plurality of the elastic wires has:
- a proximal end portion connected to the manipulation wire;
- a distal end portion opposite to the proximal end portion; and
- a maximum diameter section configured to define a maximum outer diameter of the basket section between the proximal end portion and the distal end portion;

the curved surface section has a radius of curvature that is smaller than a radius of curvature of each of the plurality of the elastic wires between the proximal end portion and the maximum diameter section;

each of the plurality of the elastic wires further has, in seriatim from the proximal end portion to the maximum diameter section, a first curved section, a second curved section, and a third curved section;

each of the first curved section, the second curved section and the third curved section has a radius of curvature that is different from the radius of the curvature of the other of the first curved section, second curved section and third curved section; and the radius of the curvature of the third curved section is smaller than the radius of curvature of the first curved section and the radius of curvature of the second curved section.

2. The endoscopic treatment instrument according to claim 1, wherein:

the sheath includes a plurality of spaced projections projecting from the distal end of the curved surface section in a direction parallel to the longitudinal axis of the sheath such that gaps are formed between the projections, arranged in a circumferential direction of the curved surface section; and the curved surface section is positioned in the gaps.

3. The endoscopic treatment instrument according to claim 2, wherein:

each of the plurality of projections includes:
- outer and inner circumferential surfaces; and
  - first and second lateral surfaces that extend radially (1) along the longitudinal axis and (2) between the outer and inner circumferential surfaces;

the lateral surfaces of adjacent of the projections that face each other define the gaps between the adjacent of the projections; and the lateral surfaces are configured such that the gaps decrease in the circumferential direction from the outer circumferential surfaces to the inner circumferential surfaces.

4. The endoscopic treatment instrument according to claim 2, wherein:

the gaps formed between the plurality of projections are arranged apart from each other in the circumferential direction, and there are fewer of the gaps than the plurality of elastic wires.

* * * * *